(12) United States Patent
Park et al.

(10) Patent No.: US 8,632,749 B2
(45) Date of Patent: Jan. 21, 2014

(54) TWO PHOTON TRACER, METHOD FOR THE PREPARATION THEREOF AND THE USE THEREOF IN SCREENING ANTICANCER AGENTS

(75) Inventors: Seung Bum Park, Seoul (KR); Bong Rae Cho, Seoul (KR); Hyang Yeon Lee, Seoul (KR); Jong Min Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 497 days.

(21) Appl. No.: 12/876,367

(22) Filed: Sep. 7, 2010

(65) Prior Publication Data

US 2011/0059022 A1  Mar. 10, 2011

(30) Foreign Application Priority Data

Sep. 7, 2009  (KR) ........................ 10-2009-0084068

(51) Int. Cl.
*A61B 5/00* (2006.01)
*A61B 8/00* (2006.01)
*A61B 10/00* (2006.01)
*A61K 49/00* (2006.01)

(52) U.S. Cl.
CPC ...................................... *A61B 5/00* (2013.01)
USPC ............................................. 424/9.1; 424/9.6

(58) Field of Classification Search
CPC ............. A61B 5/00; A61B 8/00; A61B 10/00
USPC .......................................................... 424/9.6
See application file for complete search history.

(56) References Cited

U.S. PATENT DOCUMENTS

2010/0105149 A1  4/2010  Park et al.

FOREIGN PATENT DOCUMENTS

KR  2008-0087301  10/2008

*Primary Examiner* — Michael G Hartley
*Assistant Examiner* — Melissa Perreira
(74) *Attorney, Agent, or Firm* — Hamre, Schumann, Mueller & Larson, P.C.

(57) ABSTRACT

Disclosed herein are compounds useful as two-photon tracers. Also, methods are provided for visualizing intracellular glucose uptake, screening anticancer agents, and diagnosing cancer using the compounds. They exhibit preferential uptake by cancer cells, penetrability sufficient to allow bright section images, high water solubility, high pH resistance and low toxicity in addition to applicability to living cells in deep tissues over a long period of time.

4 Claims, 15 Drawing Sheets
(6 of 15 Drawing Sheet(s) Filed in Color)

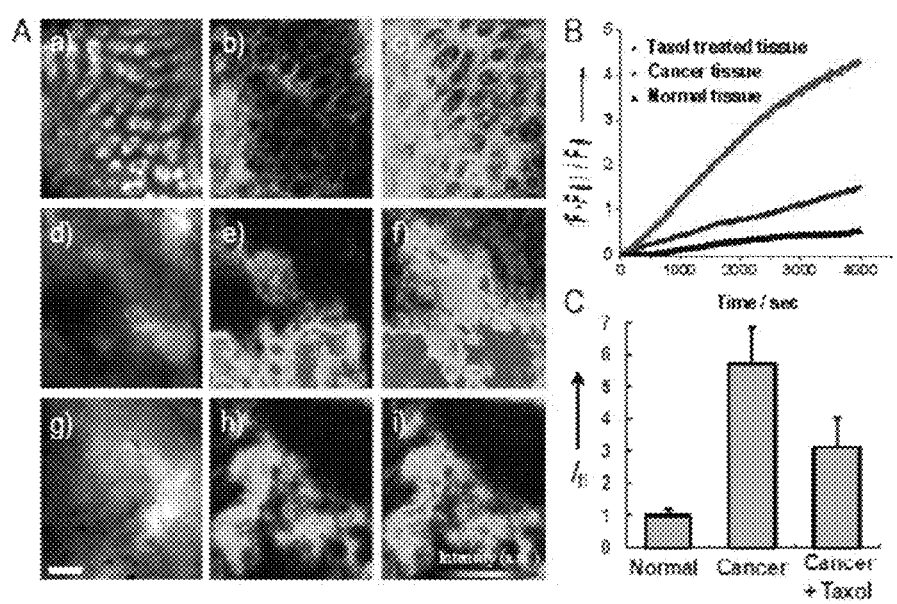

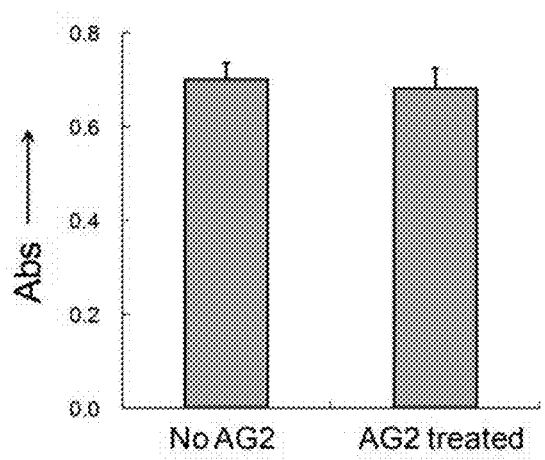

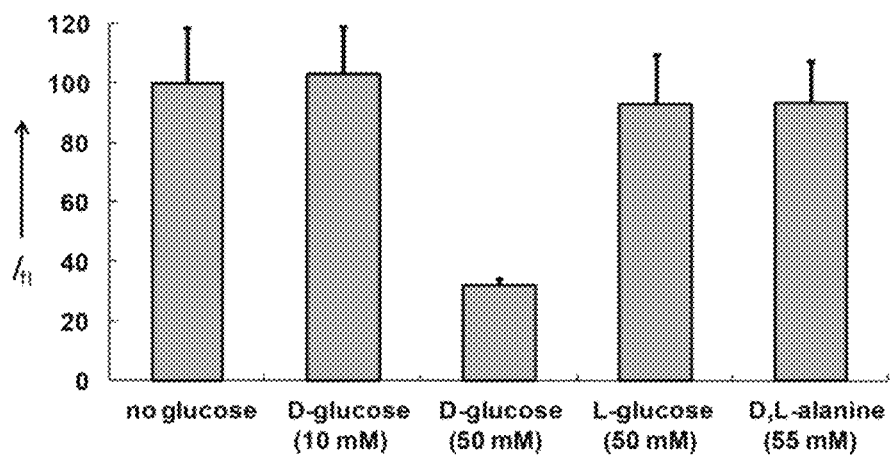

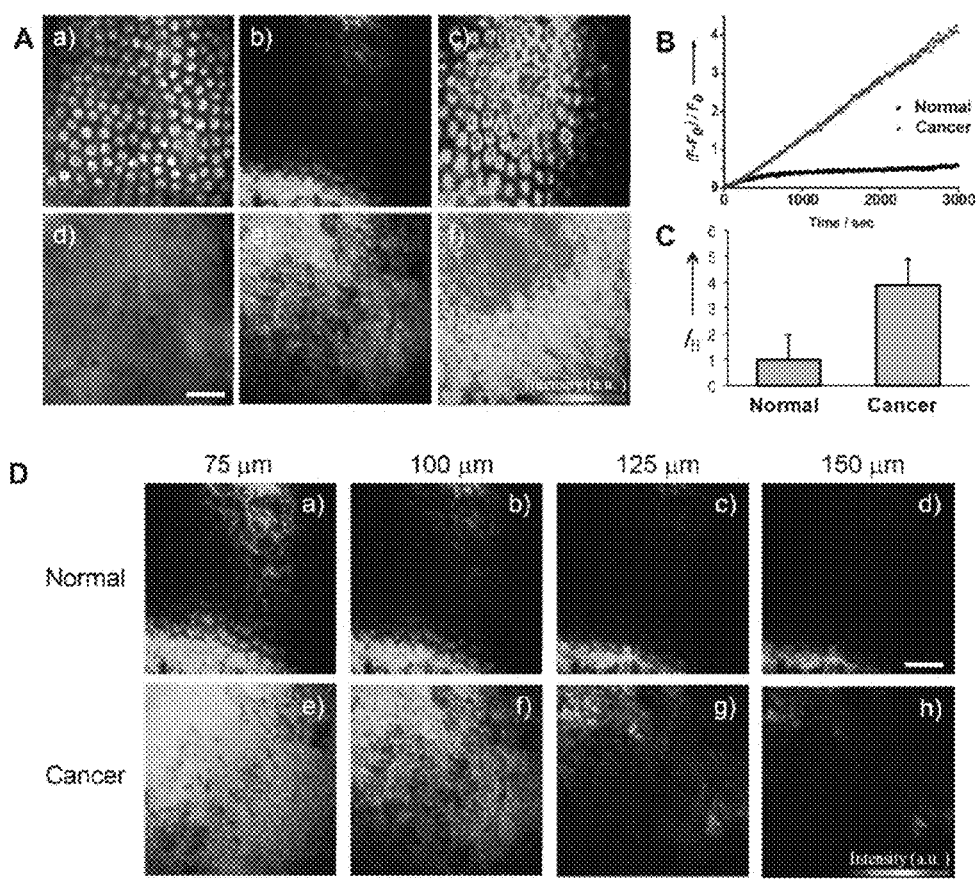

TWO PHOTON TRACER, METHOD FOR THE PREPARATION THEREOF AND THE USE THEREOF IN SCREENING ANTICANCER AGENTS

BACKGROUND OF THE INVENTION

1. Field of the Invention

The present invention relates to a compound useful as a two-photon tracer, a method for the preparation thereof, a method for the visualization of intracellular glucose uptake using the same, a method for the diagnosis of cancer using the same, and a method for screening anticancer agents using the same.

The present application claims priority from Korean Patent Application No. 10-2009-0084068 filed on Sep. 7, 2009 in the Korean Intellectual Property Office, the disclosure of which is incorporated herein by reference in its entirety.

2. Description of the Related Art

Glucose is a principal energy source essential for cell growth. Fast-growing cancer cells exhibit a high rate of glycolysis; hence, the rate of glucose uptake is faster in these cells, primarily due to overexpression or enhanced intracellular translocation of glucose transporters (GLUTs) and increased activity of mitochondria-bound hexokinases in the tumor. To monitor glucose metabolism in living systems, a variety of tracers, a variety of tracers, such as [$^{18}$F]-2-fluoro-2-deoxyglucose ($^{18}$FDG), 2-[N-(7-nitrobenz-2-oxa-1,3-diazol-4-yl)-amino]-2-deoxy-D-glucose (2-NBDG), and IR dye. 800CW-2DG, have been developed. FDG is widely used in the in vivo analysis of glucose metabolism by positron emission tomography (PEG), whereas 2-NBDG and IR dye 800CW-2DG are fluorescent probes that have been used for studying cellular metabolic functions involving GLUTs and in tumor-imaging studies.

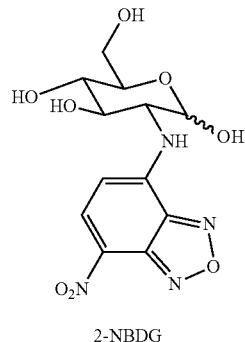 [SMILES: O=[N+]([O-])c1ccc(NC2C(O)OC(CO)C(O)C2O)c2nonc12]

2-NBDG

Recently, the present inventors developed a new fluorescent probe, cyanine-3-linked O-1-glycosylated glucose (Cy3-Glc-α), which is a better glucose probe than 2-NBDG because it can be used, without glucose starvation, to produce a much brighter image, and can be applied to the screening of anticancer agents.

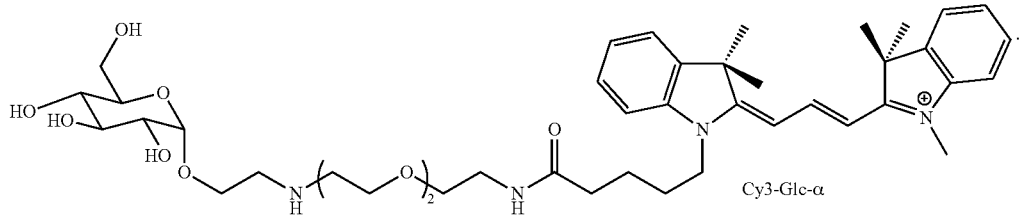

Cy3-Glc-α

In one-photon microscopy (OPM), the probes are excited with short-wavelength light (~350-550 nm); this, however, limits their applications in tissue imaging, owing to inherent problems such as shallow penetration depth (<80 μm), interference by cellular autofluorescence, photobleaching and photodamage. To overcome these problems, it is crucial to use two-photon microscopy (TPM), which utilizes two near-infrared photons for excitation. TPM offers a number of advantages over one-photon microscopy (OPM), including greater penetration depth (>500 μm), localized excitation, and longer observation times. In particular, the extra penetration depth afforded by TPM is an essential element for application in tissue-imaging studies because the artifacts arising from surface preparation, such as damaged cells, can extend over 70 μm into the tissue interior. However, visualization of glucose uptake by living cells and tissues with two-photon (TP) tracers has not been reported so far.

SUMMARY OF THE INVENTION

It is therefore an object to provide a compound useful for the visualization or quantification of glucose uptake by living cells, a method for the preparation thereof, a method for the visualization of intracellular glucose uptake using the same, a method for the diagnosis of cancer using the same, and a method for screening anticancer agents using the same.

In accordance with an aspect thereof, the present invention provides a compound having the structure represented by the following Chemical Formula 5 or 6

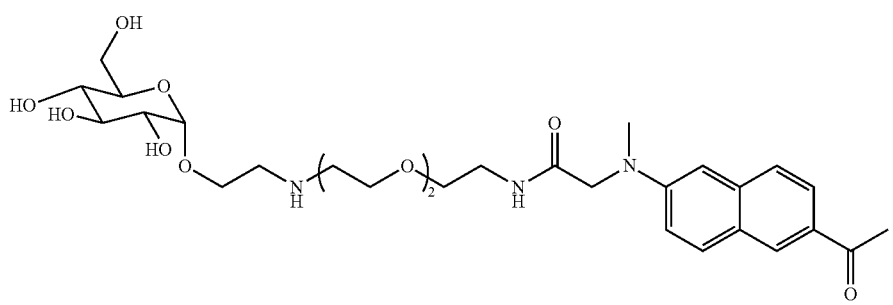

[Chemical Formula 5]

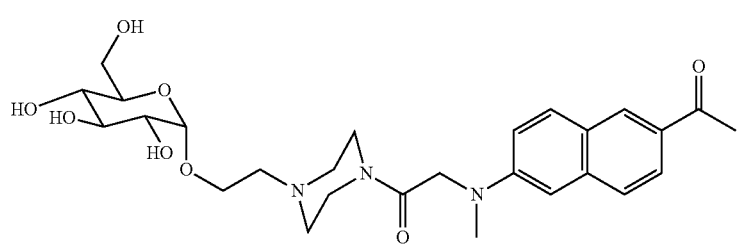

[Chemical Formula 6]

In accordance with another aspect thereof, the present invention provides a two-photon tracer comprising the structure represented above Chemical Formula 5 or 6. In accordance with a further aspect thereof, the present invention provides a method and a kit for screening an anticancer agent, applying a two-photon tracer comprising the structure of the above Chemical Formula 5 or 6 to tissues in vivo or in vitro in combination with the anticancer agent, and monitoring the tracer with TPM.

In a preferred embodiment of the present invention, an anticancer agent can be screened using TPM images obtained at different depths of penetration as measured from the surface of some tissue.

In accordance with still a further aspect thereof, the present invention provides a method and a kit for visualizing or quantifying intracellular glucose uptake, comprising the use of a two-photon tracer comprising the structure of the above Chemical Formula 5 or 6.

In a preferred embodiment of the present invention, the images are obtained at a depth of 75-150 μm from a tissue surface and the visualization or quantification may be carried out for the glucose uptake done for 3,000 s or longer.

In another preferred embodiment of the present invention, desirably, the compound of Chemical Formula 5 or 6 is used at a concentration of 100 μM or less. Higher than 100 μM of the compound may induce cell death.

In accordance with still a further aspect thereof, the present invention provides a method and a kit for diagnosing cancer cells, comprising applying a two-photon tracer comprising the structure of the above Chemical Formula 5 or 6 to cells in vivo or in vitro and monitoring the cells with TPM, thereby determining whether the cells are cancer cells or not.

In an embodiment, the cells are obtained from a cancerous tumor that is in an early stage.

In accordance with still another aspect thereof, the present invention provides a method for preparing the compound of Chemical Formula 5, comprising reaction of a compound of Chemical Formula 1 with a compound of Chemical Formula 3.

[Chemical Formula 1]

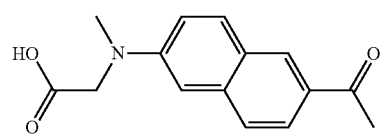

[Chemical Formula 3]

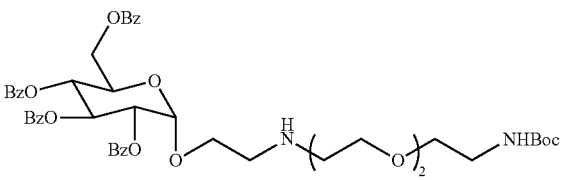

In accordance with yet another aspect thereof, the present invention provides a method for preparing the compound of Chemical Formula 6, comprising reaction of a compound of Chemical Formula 1 with a compound of Chemical Formula 4.

[Chemical Formula 1]

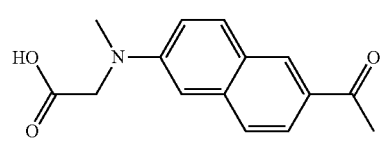

[Chemical Formula 4]

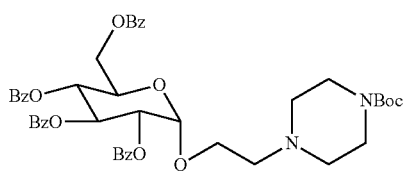

In a preferred embodiment of the present invention, the compound of Chemical Formula 4 can be obtained by reacting a compound of Chemical Formula 2 with N-Boc-piperazine.

[Chemical Formula 2]

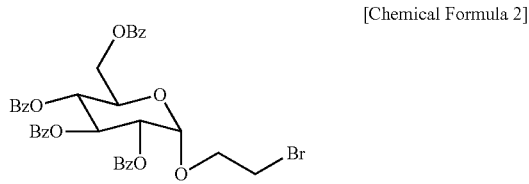

Exhibiting preferential uptake by cancer cells, a penetrability sufficient to brighten section images, high water solubility, high pH resistance and low toxicity in addition to being applicable to living cells in deep tissue over a long period of time, the compounds of the present invention are very useful as two-photon tracers.

Also, the preparation method according to the present invention is advantageous in that it can be performed by a simple process and guarantees a product that has a high production yield, selectivity and purity.

Further, the methods provided for visualizing intracellular glucose uptake, screening anticancer agents, or diagnosing cancer cells in accordance with the present invention are superior in terms of accuracy, reproductivity and safety and can be applied to living cells in deep tissues over a long period of time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will be more clearly understood from the following detailed description taken in conjunction with the accompanying drawings, in which:

FIG. 5: A) Images of normal tissue (a, b, c), cancer tissue (d, e, f), and cancer tissue treated with taxol (g, h, i). Normal tissues were incubated in ACSF for 4 hrs, and cancer tissues were incubated in the absence or presence of taxol (50 μM) in ACSF for 4 hrs, after which AG2 uptake was monitored. a, d, and g are bright-field images; b, e, and h are pseudocolored TPM images obtained after incubation with AG2 for 4000 s; and c, f, and i are pseudocolored TPM images obtained after incubation with AG2 for 4 hrs. The TPM images were obtained at a depth of 100 μm by collecting the TPEF spectra in the range of 520-620 nm upon excitation with fs pulses at 780 nm. B) The time course of AG2 uptake by normal tissue, cancer tissue, and cancer tissue treated with taxol (50 μM) at a 100 μm depth as a function of time. C) Relative AG2 uptake by normal tissue, cancer tissue, and cancer tissue treated with taxol (50 μM) for 4000 s. The columns indicate the sum of the TPEF intensities measured by photomultiplier tube at depths of 75, 100, 125, and 150 μm from the tissue surface of cancer tissue, relative to that of normal tissue. The data are the average of three independent experiments.

FIG. 7: Viability of A549 cells in the presence of AG2 as measured by using CCK-8 kit. The cells were incubated with 50 μM AG2 for 10 min.

FIG. 8: A) TPM image of A549 cells incubated with 50 μM AG2 for 10 min, B) one-photon fluorescence image of the A549 cells labeled with Mito-Tracker for 10 min, and C) merged image. Exitation wavelengths are 780 nm (a) and 488 nm (b), respectively. The images shown are representative of the images obtained in the replicate experiments (n=5). Scale bars 30 μm.

FIG. 9: Dose-dependent inhibition of AG2 uptake by A549 cells in the presence of D- and L-glucose and D,L-alanine. TPEF intensities from 40-60 cells were measured by PMT. The data are the average of at least five independent experiments. The TPEF was collected upon excitation at 780 nm with fs pulses.

FIG. 10A: Images of normal tissues (a, b, c) and cancer tissues (d, e, f) obtained from a colon cancer patient immediately after colonoscopic biopsy. a and b are bright field images; b and e are pseudo-colored TPM images obtained after incubation with AG2 (50 μM) for 3,000 s; c and f are pseudo-colored TPM images obtained after incubation with AG2 (50 μM) for 5 hrs.

FIG. 10B: Time course of AG2 uptake by normal and cancer tissues at 100 μm depth.

FIG. 10C: The columns indicate the sum of the TPEF intensities measured by PMT at depths of 75, 100, 125, and 150 μm from the tissue surface, relative to that of normal tissue. The data are the average of 3 independent experiments.

FIG. 10D: TPM images of the normal tissues (a, b, c, d) and cancer tissues (e, f, g, h) obtained by collecting the TPEF at 520-620 nm upon excitation at 780 nm with fs pulse. Scale bar, 300 μm.

DESCRIPTION OF THE PREFERRED EMBODIMENTS

Figure 1:
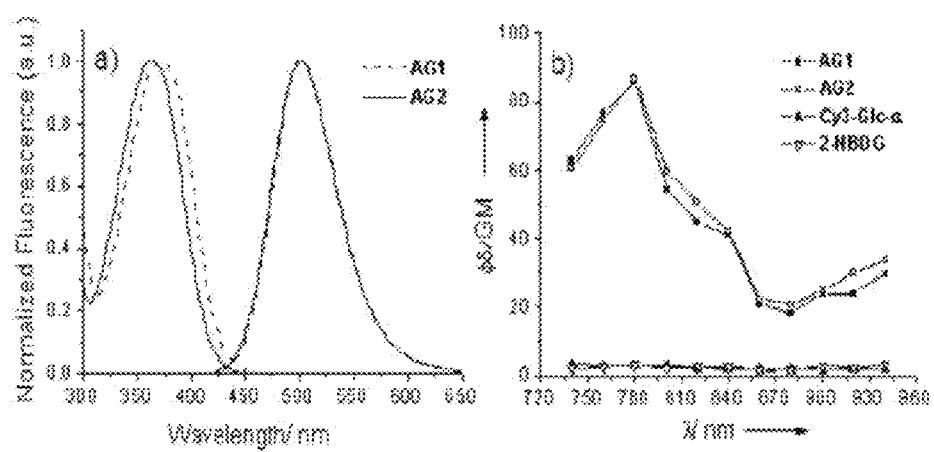
FIG. 1: (a) One-photon absorption and emission spectra of AG1 and AG2 in phosphate-buffered saline (PBS) buffer (137 mM NaCl, 3 mM KCl, 10 mM $Na_2HPO_4$, 2 mM $KH_2PO_4$, pH 7.4), (b) Two-photon action spectra for AG1, AG2, Cys3-Glc-α, and 2-NBDG in PBS buffer.

The requirements for a TP tracer to visualize glucose uptake include sufficient water solubility for staining cells and tissues, preferential uptake by cancer cells, a large TP cross-section for a bright TPM image, pH resistance, and high photostability.

The strategy of the present invention is to link α-D-glucose with the fluorophore 2-acetyl-6-dimethylaminonaphthalene (acedan) through a 3,6-dioxaoctan-1,8-diamine (AG1) or a piperazine (AG2) linkage, so that the tracers are transported into the cells through the glucose-specific mechanism. Acedan is a polarity-sensitive fluorophore that has been successfully employed in the development of TP probes for the cell membrane, metal ions, and acidic vesicles. The disclosure of the present invention has it that that these tracers facilitate the visualization of glucose uptake in cancer cells and live tissues at a depth of 75-150 μm for 3,000 s or longer and can be used for screening anticancer agents.

The preparation of AG1 and AG2 is illustrated in Reaction Scheme 1. 6-Acetyl-2-[N-methyl-N-(carboxymethyl)amino]naphthalene (1), compound 2, and compound 3 were prepared as previously reported. The reaction of compound 2 with N-Boc-piperazine afforded compound 4 in 70% yield. AG1 and AG2 were prepared in 26% and 86% yields, respectively, by treating compound 3 and compound 4 with compound 1.

molecules as polarity probes. Moreover, they are pH insensitive in the biologically relevant pH range. The TP action spectrum of AG1 determined by the two-photon excited fluorescence (TPEF) method indicated a Φδ value of approximately 90 GM at 780 nm, which is much larger than those observed for Cy3-Glc-α and 2-NBDG. Thus, the TPM images of the samples stained with AG1 or AG2 would appear much brighter than those stained with Cy3-Glc-α or 2-NBDG.

TABLE 1

Photophysical Data for AG1, AG2, Cy3-Glc-α and 2-NBDG

| Compound | $\lambda^{(1)}_{max}/\lambda^{1}_{max}$[b] | Φ[c] | $\lambda_{max}$[d] | $\delta_{max}$[e] | $\Phi\delta_{max}$[f] |
|---|---|---|---|---|---|
| AG1 | 373/501 | 0.90 | 780 | 95 | 86 |
| AG2 | 375/501 | 0.56 | 780 | 155 | 88 |
| Cy3-Glc-α | 545/555 | 0.01 | n.d.[g] | n.d.[g,h] | n.d.[g,h] |
| 2-NBDG | 465/540[i] | n.d.[g] | n.d.[g] | n.d.[g,h] | n.d.[g,h] |

[a]All measurements were performed in a PBS buffer.
[b]$\lambda_{max}$ values of the one-photon absorption and emission spectra (nm).
[c]Fluorescence quantum yield, ±15%.
[d]$\lambda_{max}$ of the two-photon absorption spectrum (nm).
[e]The peak two-photon action cross-section (10$^{-50}$ cm$^4$/photon(GM), ±15%).
[f]Two-photon action cross-section (GM).
[g]n.d.: not determined.
[h]The two-photon-excited fluorescence intensity was too weak to allow accurate measurement of the cross-section.
[i]*The Handbooks-A Guide to Fluorescent Probes and Labeling Techonologies*, 10$^{th}$ ed. R. P. Haugland, Ed.; Molecular Probes: Eugene, OR, 2005.

The optimum concentration of these probes for the cellular uptake experiments was determined by comparing the TPM images of A549 cells treated with 6, 12.5, 25, 50, and 100 μM of AG1 and AG2 for 30 min. The TPM images appeared brighter as the probe concentration was increased up to 50 μM; however, at a concentration of 100 μM, some cell death was observed. Moreover, a higher uptake rate and a brighter TPM image were obtained when the cells were treated with AG2 than when they were treated with AG1. Furthermore, the effect of AG2 on the viability of cells was studied by using the CCK8 kit: AG2 showed negligible toxicity, which indicates

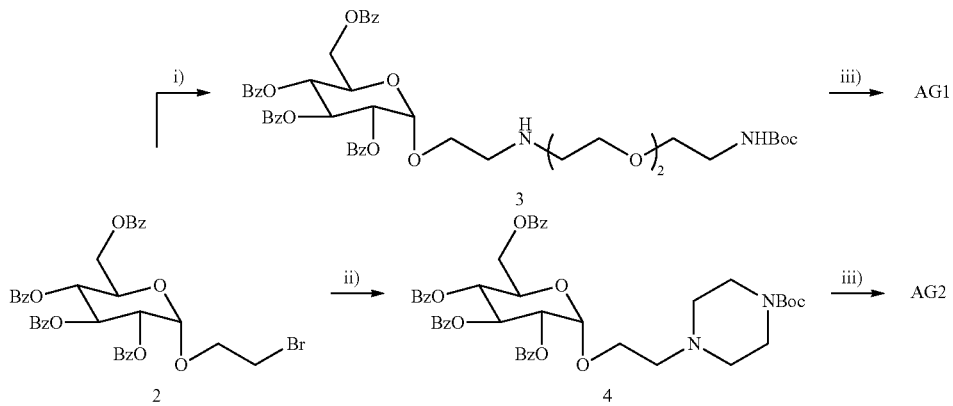

Scheme 1: (i) N-Boc-3,6-dioxaoctane-1,8-diamine, Et$_3$N, DMF, 50° C.
(ii) N-Boc-peperazine, Et$_3$N, DMF, 50° C.
(iii) (a) NaOMe, MeOH; (b) 50% TFA/DCM; (c) 1, EDC, DIPEA, DMF.

The fluorescence spectra of AG1 and AG2 showed gradual bathochromic shifts with increases in solvent polarity ($E_T^N$) with the following order of solvents: 1,4-dioxane<DMF<EtOH<H$_2$O. The large bathochromic shifts upon increasing solvent polarity indicate the utility of these that it could be applied for live-cell imaging. Therefore, 50 μM AG2 was used as the optimum concentration in further cellular uptake experiments.

Figure 2:
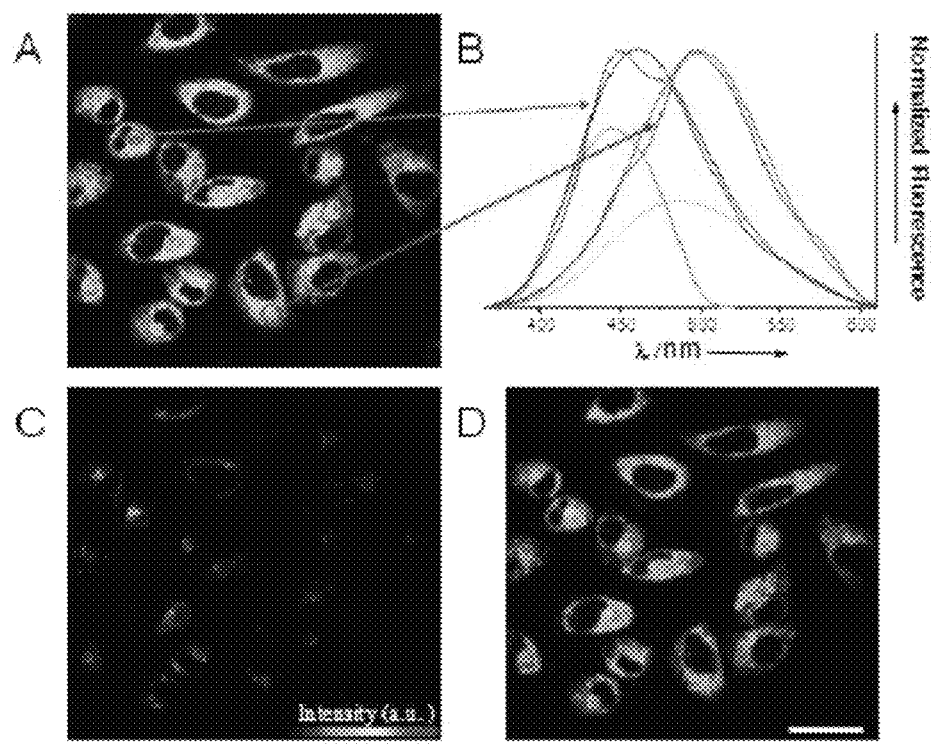
FIG. 2: Pseudocolored TPM images of A549 cells incubated with 50 μM AG2 for 10 min, collected at A) 360-620, C) 360-460, and D) 520-620 nm. B). Two-photon-excited fluorescence spectra from the hydrophobic (marked in blue) and hydrophilic (marked in red) regions of the AG2-labeled A549 cells. The thin pale blue and pink curves represent the dissected Gaussian functions for the blue and red bands, respectively. The excitation wavelength was 780 nm. The images shown are representative of the images obtained in the repeated experimentation (n=5). Scale bar: 30 μM.

The pseudocolored TPM images of cultured A549 cells treated with 50 μM AG2 showed intense spots and homogeneous domains with two-photon emission maxima at 461 (marked in blue) and 497 nm (marked in red) (see FIGS. 2A and 2B). The TPEF spectrum of the intense spots was asymmetrical and could be fitted to two Gaussian functions with emission maxima at 445 (green line) and 488 nm (orange line), whereas the TPEF spectrum of the homogeneous domain could be fitted to a single Gaussian function (pink line) with an emission maximum at 497 nm. It is noticeable that the longer wavelength band of the dissected Gaussian function (orange line) is similar to the band of the single Gaussian function (pink line). This result suggests that the probe is located in two regions of different polarity: a more polar one that is likely to be cytosol and a less polar one that is likely to be membrane associated. Moreover, the shorter wavelength band (green line) in the dissected Gaussian functions decreases to the baseline at wavelengths of less than 520 nm. Consistently, the TPM image collected at 520-620 nm is homogeneous without intense spots, whereas the one collected at 360-460 nm clearly shows intense spots. Similar results were reported for acedan-derived TP probes for $Mg^{2+}$ (AMg1) and $Ca^{2+}$ ions (ACa1). Therefore, cytosolic AG2 can be selectively detected by using the detection window of 520-620 nm, with minimal interference from the membrane-bound probes. Furthermore, the TPM images of A549 cells co-stained with AG2 and MitoTracker, a well-known one photon fluorescent (OPF) probe for mitochondria, merged well with the OPM image (see FIG. 2), which indicates that the probes are predominantly located in the mitochondria.

In order to assess whether AG2 is selectively taken up by cancer cells, the efficiencies of AG2 uptake by A549 (lung carcinoma cell line), HeLa (cervical cancer cell line), HEK293 (human embryonic kidney 293 cell line), and NIH/3T3 (murine fibroblast cell line) cells were compared. AG2 uptake was observed to be most efficient in A549 and HeLa cells, followed by HEK293 and NIH/3T3 cells (see FIG. 3B); this result is similar to that obtained in the case of Cy3-Glc-α, confirming the selective uptake of AG2 by the cancer cells with enhanced glucose metabolism. The cellular uptake experiment showed that AG2 effectively competes with D-glucose in the media for cellular uptake; the fluorescence intensities of AG2 in A549 cells inoculated with media containing 10 mM or 50 mM D-glucose were reduced by about 16 and 74%, respectively, as compared to that with the glucose-depleted medium, and the fluorescence intensity was not affected by medium containing L-glucose (50 mM, see figures). Furthermore, AG2 uptake was not influenced by the presence of 55 mM D-/L-alanine, which indicates that osmotic pressure does not have an impact on AG2 uptake. These results suggest that AG2 is a glucose analogue that is taken up by the cells through a glucose-specific transport system and not by passive diffusion. Therefore, AG2 can be used for visualizing glucose uptake in living cells by TPM, without subjecting the cells to glucose starvation.

Figure 4:
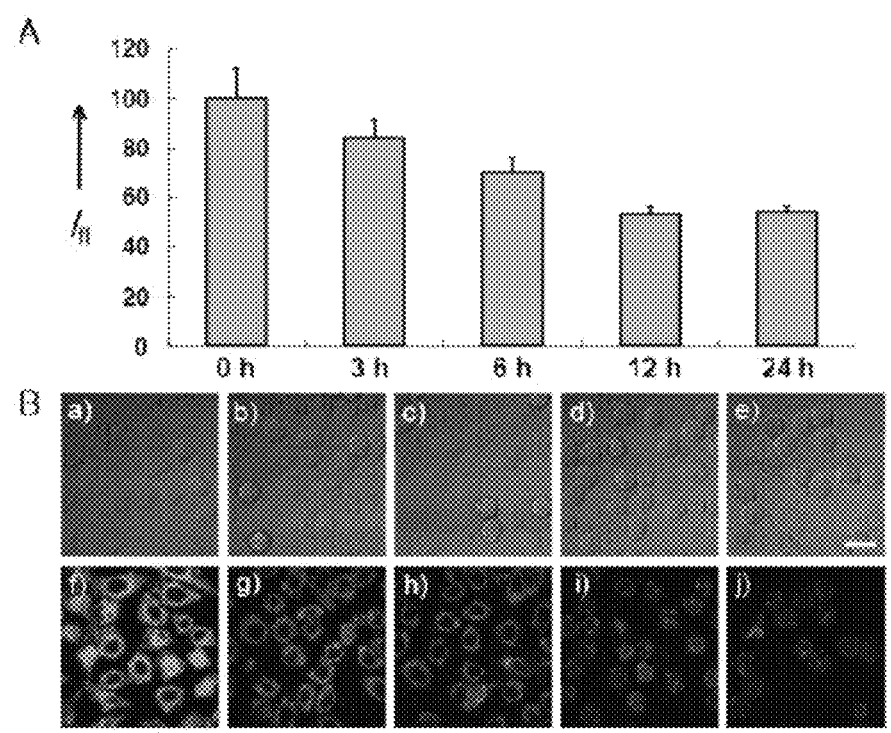
FIG. 4: (A) Relative AG2 uptake by A549 cells after treatment with taxol (9.8 μM) for 0, 3, 6, 12, and 24 hrs. TPEF intensities from 40-60 cells were determined by photomultiplier tube (PMT). The data are the average of at least five independent experiments. (B) TPM images of A549 cells after treatment with taxol for 0 h (a, f), 3 h (b, g), 6 h (c, h), 12 h (d, i), and 24 h (e, j). a-e are bright field images and f-j are TPM images. Each image was obtained after treating the cells with taxol for the designated period of time, after which they were incubated with AG2 (50 μM) for 10 min. The images were obtained by collecting the TPEF in the range of 520-620 nm upon excitation with fs pulses at 780 nm. The images shown are representative of the images obtained in the repeated experiments (n=5). Scale bar, 30 μm.
Figure 6A:
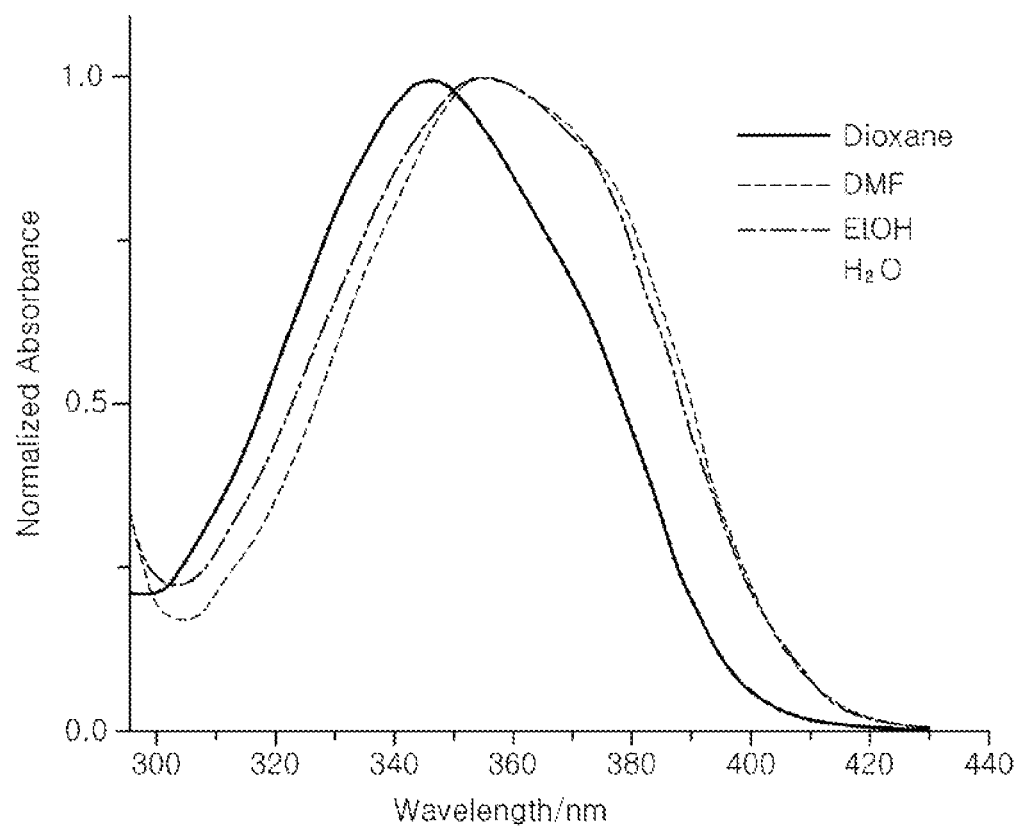
FIGS. 6a-6f: Absorption spectra were recorded on a Hewlett-Packard 8453 diode array spectrophotometer, and fluorescence spectra were obtained with Amico-Bowman series 2 luminescence spectrometer with a 1-cm standard quartz cell. The fluorescence quantum yield was determined by using Coumarin 307 and Rhodamine B as the reference. The spectral data obtained under various conditions is summarized in FIGS. 6a-6f and Table 3.
Figure 6B:
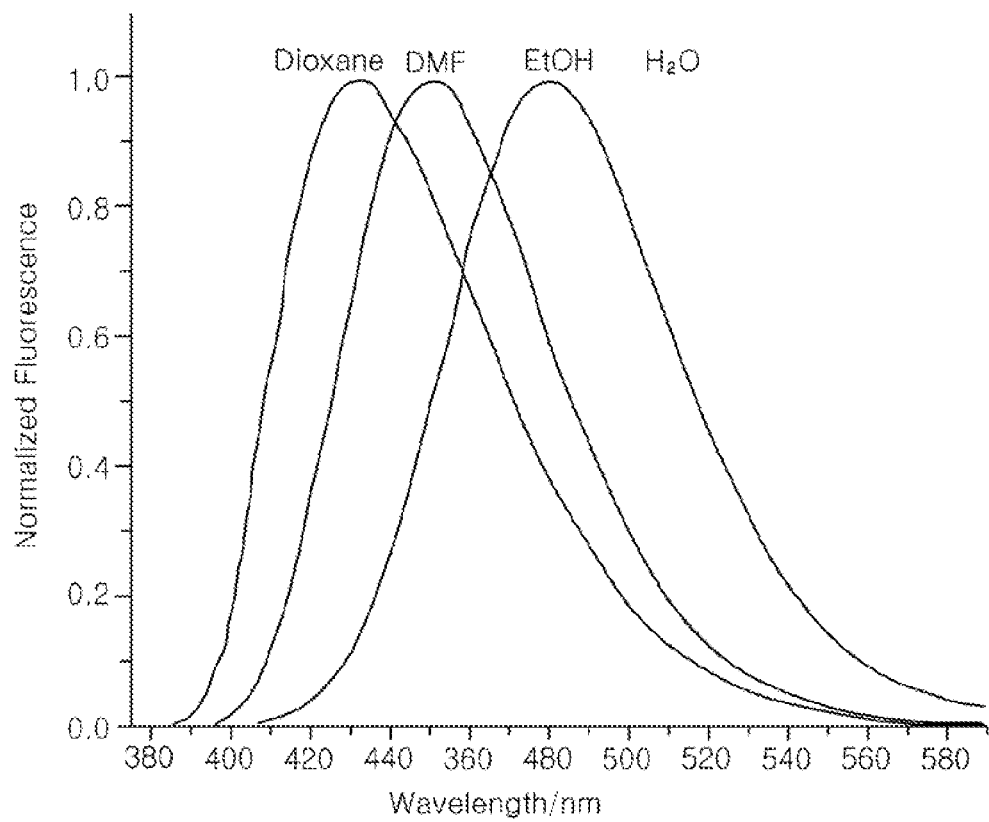
Figure 6C:
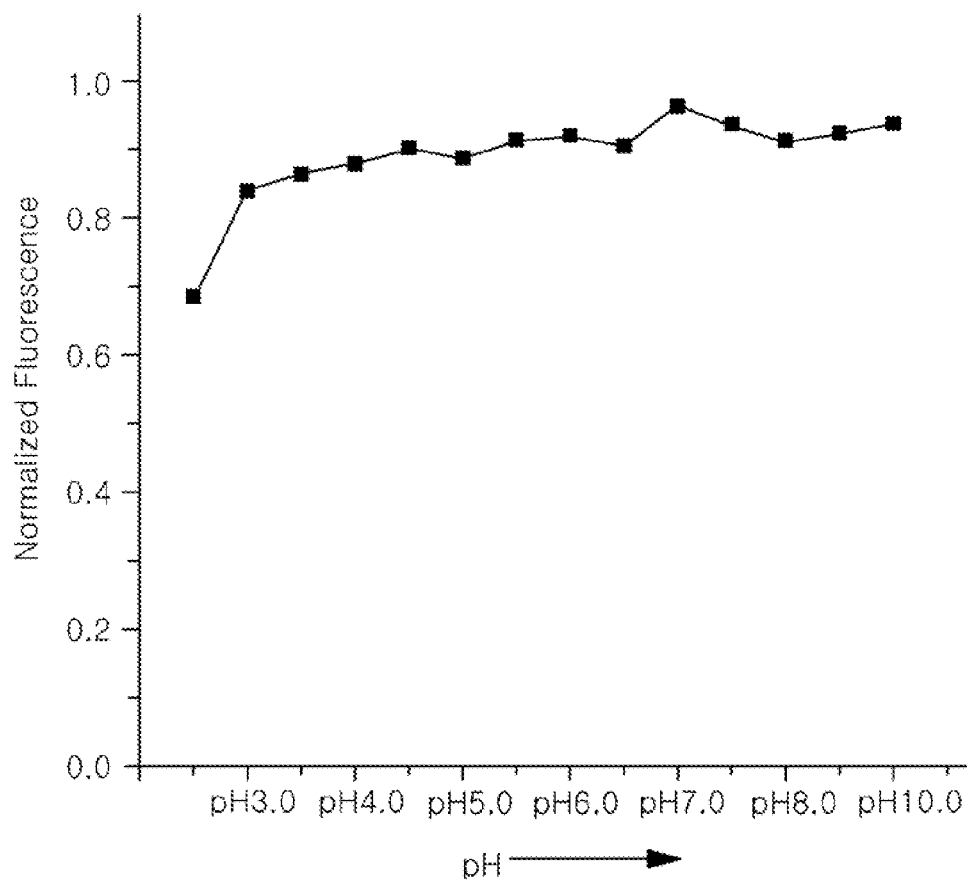
Figure 6D:
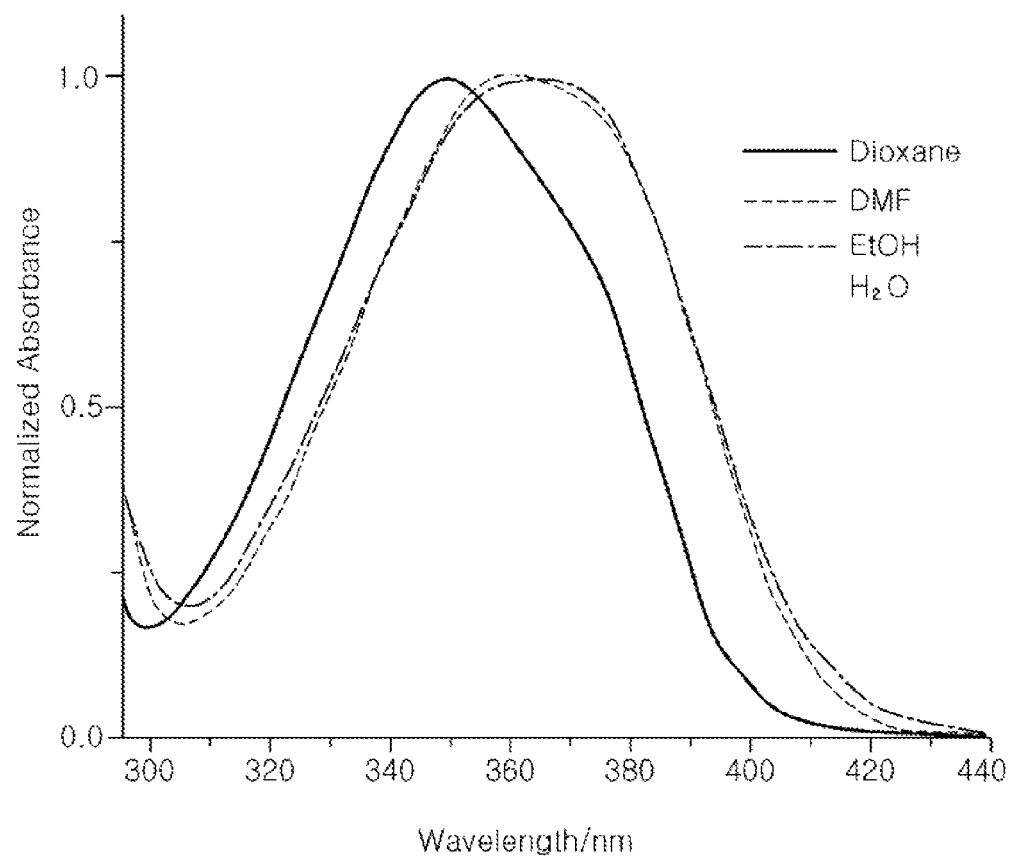
Figure 6E:
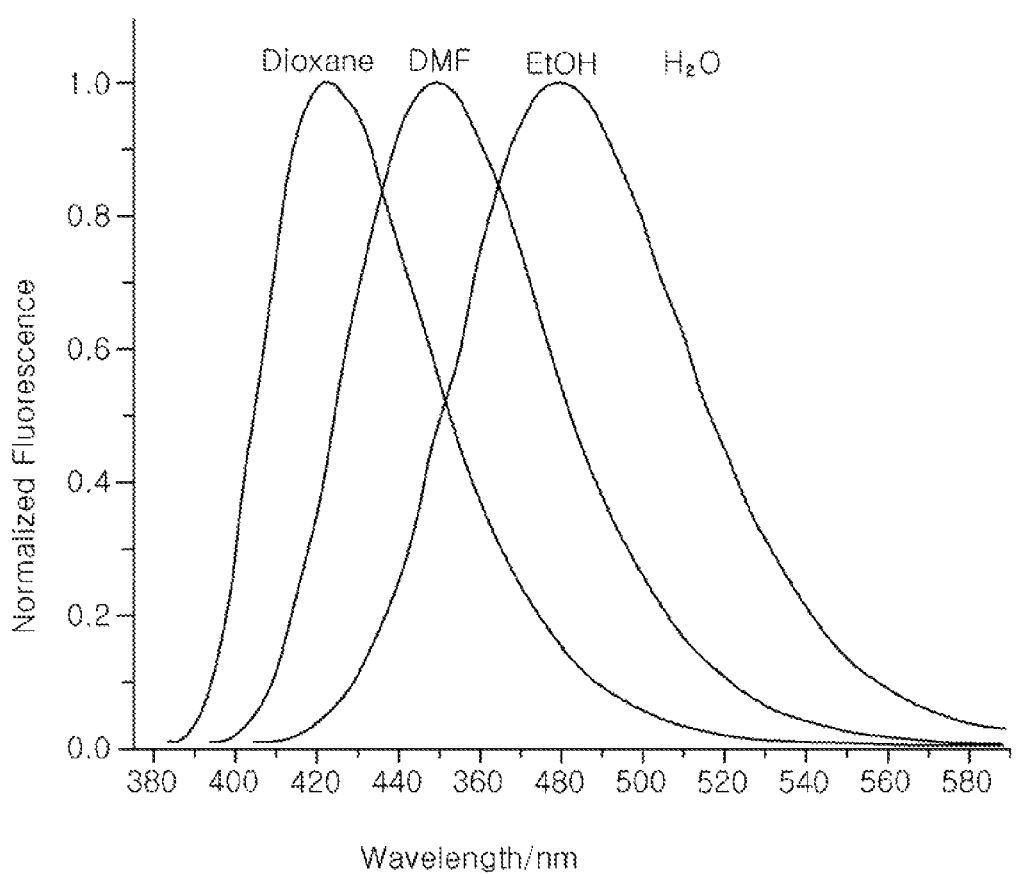
Figure 6F:
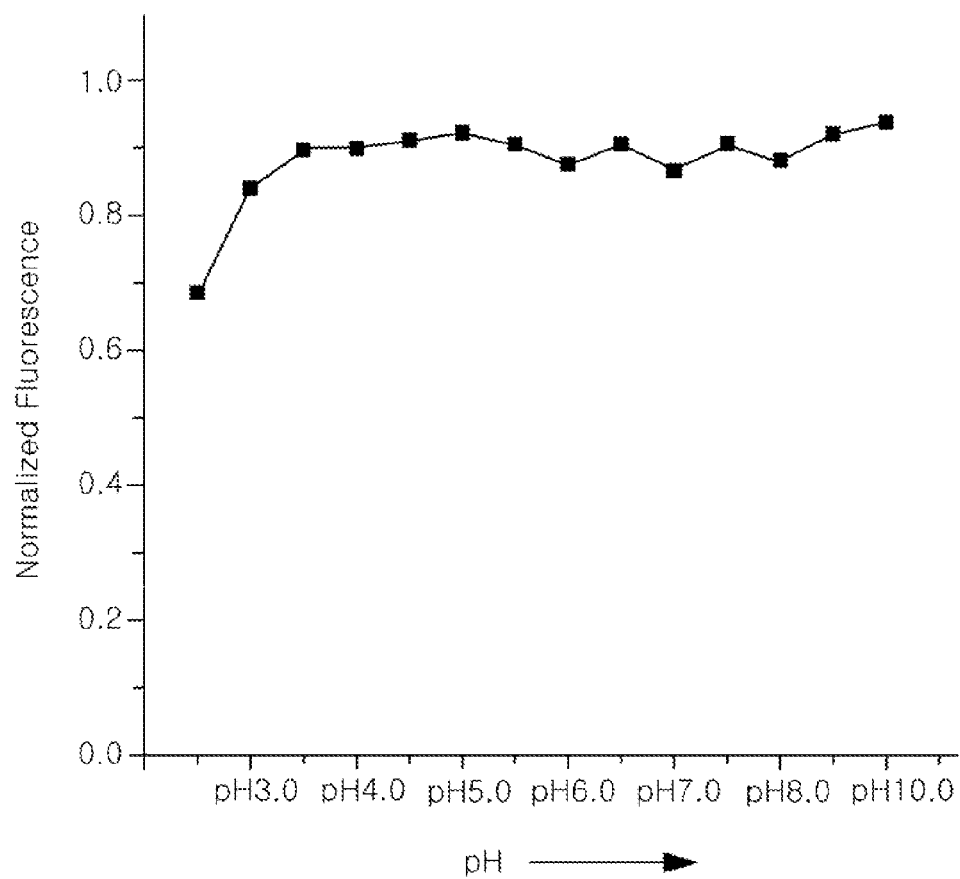
Figure 6:
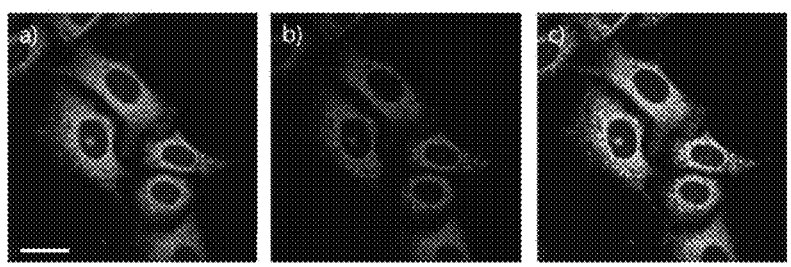

In demonstrate the utility of this probe, an analysis was made of the effects of taxol on AG2 uptake by A549 cells. It was expected that the anticancer agent would depress the cellular metabolism and thereby reduce glucose uptake in the cancer cells. The cells were incubated with the anticancer agent for 1, 3, 6, 12, and 24 h, washed with PBS, treated with AG2, and then imaged. The cellular uptake of AG2 was lower with longer incubation times (see FIG. 4). The uptake of AG2 was also observed in a dose-dependent pattern with taxol concentrations of 49 nM, 490 nM, and 9.8 µM (Table 2). Another anticancer agent, combretastatin, also inhibited AG2 uptake in a similar manner (Table 2). Hence, AG2 can be used for screening anticancer agents in living cells using TPM.

TABLE 2

Dose Dependence of AG2 Uptake by A549 in the Presence of Various Concentrations of Anticancer Agents

|  | After 6 h | After 12 h |
|---|---|---|
| Taxol (9.8 µM) | 69.5% | 50.7% |
| Taxol (49 nM) | 89.6% | 69.5% |
| Taxol (49 nM) | 96.7% | 81.8% |
| Combrestastatin (2 µM) | 70.2% | 53.2% |

In the present invention, an additional assessment was made of the utility of AG2 in tissue imaging for the diagnosis of colon cancer. In this regard, the images of normal- and cancer-tissue slices from colon-cancer patients were employed. The bright-field image of the normal tissue clearly revealed the presence of glands on the tissue surface. In contrast, the cancer tissue appeared almost amorphous and did not have a definite structure (see FIG. 5A). The tissues were incubated in artificial cerebrospinal fluid (ACSF) for 4 h at 37° C. in the absence and presence of taxol (50 µM), after which AG2 uptake was monitored with TPM by following the change in TPEF at a depth of 100 µm.

The results show that AG2 uptake in cancer tissue is much faster than in the normal tissue and that the cancer tissue pretreated with taxol for 4 hrs exhibits much slower AG2 uptake than the untreated one (see FIGS. 5A and 5B). A similar result was observed from normal- and cancer-tissue slices obtained immediately after colonoscopic biopsy, which indicates that incubation of the tissue slices in ACSF for 4 h did not significantly influence the relative uptake rate. Furthermore, the uptake could be monitored for more than 3000 s without noticeable decay.

These results strongly support the applicability of AG2 in deep-tissue imaging for the diagnosis of colon cancer, in addition to its useful properties for in vivo imaging, namely high photostability and low toxicity.

Colon cancer is known to originate from the mucosa in the intestinal glands and spread into the interior of the tissue. In the present invention, TPM images were obtained at different depths from the tissue surface. The TPEF intensities appear scattered at shallow depths due to different degrees of dye adsorption at tissue surfaces (see the bright field images of the figures). However, reliable results could be obtained at a depth of ≥75 µm from the tissue surface. TPM images of the tissue sections obtained for 4000 s revealed the AG2 distribution at depths of 75, 100, 125, and 150 µm, and each image exclusively represents the distribution in a given plane.

It is noticeable that TPM images were obtained up to a depth of 150 µm due to the limited penetration of AG2 into the tissues during the incubation. If the tissues were incubated for a longer period of time, TPM images at deeper depths could be obtained. The uptake was most efficient near the tissue surface; it decreased with larger imaging depths and was negligible at a depth of >150 µm.

In addition, the uptake rate was much slower than that in the cells, probably because of the extracellular matrix, which is more abundantly found in aged tissues. The sum of the TPEF intensities measured at depths of from 75 to 150 µm was largest in the case of cancer tissue, followed by cancer tissue treated with taxol, and then normal tissue (see figures). This result once again clearly demonstrates the preferential uptake of AG2 by cancerous tissue and emphasizes the usefulness of AG2 in the diagnosis of colon cancer.

The compounds effective for use as TP tracers in accordance with the present invention are pH independent in a wide range of physiological pH values (pH 4.0-10), and may be useful in diagnosing the early stages of cancer and in the development of customized cancer therapies for patients by comparing the uptake rates thereof in normal and cancer tissue treated with different anticancer agents at different depths.

A better understanding of the present invention may be obtained through the following examples which are set forth to illustrate, but are not to be construed as limiting the present invention.

EXAMPLES

Preparation of Two-Photon Tracer According to the Present Invention

6-Acetyl-2-[N-methyl-N-(carboxylmethyl)amino]naphthalene (compound 1), (2-bromoethyl)-2,3,4,6-tetra-O-benzoyl-α-D-glucoside (compound 2) and [2-(N-Boc-3,6-dioxaoctane-1,8-diaminoethyl)]-2,3,4,6-tetra-O-benzyol-α-D-glucoside (compound 3) were prepared as previously shown. Below, a description is given of the syntheses of AG1, AG2, and compound 4.

Example 1

Synthesis of AG1

To a solution of compound 3 (130 mg, 0.17 mmol) in MeOH (1 mM), sodium methoxide (0.5 M in MeOH, 1.1 mL, 0.56 mmol) was added for debenzoylation of compound 3. After the reaction was completed, the reaction mixture was neutralized with methanolic HCl, and then concentrated under reduced pressure. For the deprotection of the Boc group, 50% TFA in dichloromethane was added to the residue resulting from the previous reaction. The resulting fully-deprotected compound was condensed by $N_2$ purging, re-dissolved in DMF (1 mL), and slightly basified with TEA (0.58 mL, 0.42 mmol), followed by the addition of compound 1 (36 mg, 0.14 mmol) and EDC (40 mg, 0.21 mmol) to the DMF (500 μL) for amide coupling. The reaction mixture was stirred at room temperature and reaction completion was monitored by HPLC analysis.

The elution protocol for analytical HPLC started with 95% eluent A (deionized water containing 0.1% TFA) and 5% eluent B (HPLC-grade acetonitrile containing 0.1% TFA) for 1 min, followed by a linear gradient to 60, 50, 5, and 0% of eluent A over the period of 4, 10, 10, and 5 min, respectively. The elution continued using 0% eluent A for 5 min and returned back to 95% eluent A over a 10 min period to allow for regeneration. Purification by prep-HPLC afforded 22 mg (26%) of AG1 (retention time: 11 min). The desired product was confirmed by $^1H$, $^{13}C$ NMR, MALDI-TOF MS, and HRMS.

$^1H$ NMR (300 MHz, $CD_3OD$) δ 8.40 (s, 1H), 7.89 (s, 1H), 7.86 (s, 1H), 7.66 (d, J=8.7 Hz, 1H), 7.18 (dd, J=6.6, 2.4 Hz, 1H), 6.97 (d, J=2.1 Hz, 1H), 4.82 (d, J=3.6 Hz, 1H), 4.10 (s, 2H), 4.00-3.93 (m, 1H), 3.81 (dd, J=11.7, 2.0 Hz, 1H), 3.70-3.58 (m, 5H), 3.57-3.47 (m, 8H), 3.45-3.35 (m, 3H), 3.32-3.27 (m, 3H), 3.25-3.22 (m, 2H), 3.15-3.12 (m, 2H), 2.64 (s, 3H);

$^{13}C$ NMR (75 MHz, $CD_3OD$) δ 198.94, 171.66, 149.45, 137.66, 130.84, 130.64, 130.49, 126.16, 125.68, 123.94, 116.04, 105.69, 98.84, 73.53, 72.89, 71.83, 70.14, 69.97, 69.84, 69.20, 65.36, 62.26, 61.23, 56.32, 46.92, 46.87, 38.80, 38.70, 25.08; HRMS ($FAB^+$) calcd for $C_{29}H_{44}N_3O_{10}$ $[M+H]^+$: 594.3021; found: 594.3020.

Example 2

Synthesis of Compound 4 [2-(N-Boc-piperazinyl)]-2,3,4,6-tetra-O-benzoyl-α-D-glucoside Compound 4 was prepared in a manner similar to that used for the synthesis of compound 3 from compound 2. To a solution of compound 2 (230 mg, 0.327 mmol) in 2 mL of anhydrous DMF were added N-Boc-piperazine (183 mg, 0.981 mmol) and TEA (182 μL, 1.308 mmol), and the reaction mixture was stirred at 50° C. After reaction completion was monitored with TLC, the resulting solution was diluted with $ddH_2O$, and extracted with ethyl acetate. The combined organic layer was washed with brine and dried under anhydrous $MgSO_4$. The filtrate was condensed under reduced pressure, followed by purification through silica-gel flash column chromatography (n-hexane:ethyl acetate=2:1 gradually changed to 1:2) to produce the desired product 4 as a yellowish oil (185 mg, 70%):

$^1H$ NMR (500 MHz, $CDCl^3$) δ 8.05-7.86 (m, 8H), 7.57-7.28 (m, 12H), 6.18 (t, J=10 Hz, 1H), 5.68 (t, J=9.5 Hz, 1H), 5.43 (d, J=3.5 Hz, 1H), 5.29 (dd, J=10.0, 3.5 Hz, 1H), 4.63-4.59 (m, 1H), 4.49-4.45 (m, 2H), 3.89 (ddd, J=11.0, 5.5, 5.0 Hz, 1H), 3.67 (ddd, J=11.0, 6.0, 5.0 Hz, 1H), 3.23 (bs, 4H), 2.65-2.58 (m, 2H), 2.35 (bs, 4H), 1.44 (s, 9H);

$^{13}C$ NMR (125 MHz, $CDCl_3$) δ 166.62, 166.30, 166.16, 165.78, 155.11, 133.99, 133.92, 133.64, 130.33, 130.20, 130.16, 130.13, 129.62, 129.44, 129.34, 128.97, 128.90, 128.78, 96.38, 96.32, 80.01, 72.42, 70.88, 70.00, 68.73, 66.73, 63.51, 57.92, 53.87, 28.91; LC/MS calcd for $C_{45}H_{49}N_2O_{12}$ $[M+H]^+$: 809; found: 809.

Example 3

Synthesis of AG2

AG2 was prepared in a procedure similar to that used for the synthesis of AG1. The crude product was purified by prep-HPLC to afford 13 mg (86%) of AG2.

$^1H$ NMR (300 MHz, $CD_3OD$) δ 8.41 (s, 1H), 7.89-7.83 (m, 2H), 7.64 (d, J=8.0 Hz, 1H), 7.21 (dd, J=9.3, 2.3 Hz, 1H), 6.98 (s, 1H), 4.92 (d, J=3.6 Hz, 1H), 4.54 (s, 2H), 4.18-4.07 (m, 2H), 3.88-3.83 (m, 3H), 3.71-3.43 (m, 10H), 3.35-3.32 (m, 2H), 3.17 (s, 4H), 2.65 (s, 3H);

$^{13}C$ NMR (75 MHz, $CD_3OD$) δ 198.96, 168.82, 149.77, 137.84, 130.54, 130.47, 125.98, 125.38, 123.76, 115.87, 105.28, 98.93, 73.49, 73.10, 71.72, 70.01, 61.23, 60.47, 56.01, 52.92, 38.41, 25.01; HRMS ($FAB^+$) calcd for $C_{27}H_{38}N_3O_8[M+H]^+$: 532.2653; found, 532.2652

Experimental Examples

Experimental Example 1

Spectroscopic Measurements

Absorption spectra were recorded on a Hewlett-Packard 8453 diode array spectrophotometer, and fluorescence spectra were obtained with Amico-Bowman series 2 luminescence spectrometer with a 1-cm standard quartz cell. The fluorescence quantum yield was determined by using Coumarin 307 and Rhodamine B as the reference. The spectral data obtained under various conditions are summarized in FIGS. 6a-6f and Table 3.

TABLE 3

Photophysical Properties of AG1, AG2 in Various Solvents.

| Solvent ($E_T^N$)[a] | $\lambda^{(1)}_{max}$[b] | | $\lambda^1_{max}$[b] | | $\Phi$[c] | |
|---|---|---|---|---|---|---|
| | AG1 | AG2 | AG1 | AG2 | AG1 | AG2 |
| Dioxane(0.164) | 360 | 362 | 434 | 425 | 0.59 | 0.72 |
| DMF(0.386) | 366 | 369 | 451 | 449 | 1.00 | 1.00 |
| EtOH(0.654) | 364 | 370 | 479 | 480 | 1.00 | 0.97 |
| H2O(1.00) | 373 | 375 | 501 | 501 | 0.90 | 0.56 |

[a]The numbers in parentheses are the normalized empirical parameters of solvent polarity.[5]
[b]$\lambda_{max}$ of the one-photon absorption and emission spectra in nm.
[c]Fluorescence quantum yield, ±15%.

Experimental Example 2

Measurement of Two-photon Cross Section

The two-photon cross section (δ) was determined using the femto second (fs) fluorescence measurement technique as described previously. AG1, AG2, Cy3-Glc-α, and 2-NBDG were dissolved in 30 mM PBC buffer (137 mM NaCl, 3 mM KCl, 10 mM $Na_2HPO_4$, 2 mM $KH_2PO_4$, pH 7.4) at a concentration of $5.0\times10^{-6}$ M and then the two-photon induced fluorescence intensity was measured at 740-940 nm by using fluorescein ($8.0\times10^{-5}$ M, pH=11) as the reference, whose two-photon property has already been well characterized. The intensities of the two photon induced fluorescence spectra of the reference and sample emitted at the same excitation wavelength were determined.

The TPA cross section was calculated according to Eq. 1, $$\delta = \frac{S_s \Phi_r \phi_r c_r}{S_r \Phi_s \phi_s c_s} \delta_r \quad (1)$$

wherein
the subscripts s and r stand for the sample and reference molecules;
S denotes the intensity of the signal collected by a CCD detector;
Φ is the fluorescence quantum yield.
φ is the overall fluorescence collection efficiency of the experimental apparatus;
c denotes the numerical density of the molecules in solution; and
$\delta_r$ is the TPA cross section of the reference molecule.

The results are shown in FIG. 1 and the above-described Table 1.

Experimental Example 3

Two-photon Fluorescence Microscopy

Two-photon fluorescence microscopy images of probe-labeled cells and tissues were obtained with a spectral confocal microscope (Leica TCS SP2) with a ×100 (NA-1.30 OIL) objective lens and a multiphoton microscope (Leica TCS SP2) with a ×20 (NA=0.30 DRY) objective lens.

The two photon fluorescence microscopy images were obtained with a DM IRE2 Microscope (Leica) by exciting the probes with a mode-locked titanium-sapphire laser source (Coherent Chameleon, 90 MHz, 200 fs) set at a wavelength of 780 nm and an output power of 1230 mW, (which corresponded to approximately 10 mW average power in the focal plane).

In order to obtain images in the 360-460 nm and 520-620 nm range, internal PMTs were used to collect the signals in an 8 bit unsigned 512×512 pixels at 400 Hz scan speed.

Experimental Example 4

Cell Culture and Imaging

A549 human lung carcinoma cells, HeLa human cervical carcinoma cells, NIH/3T3 murine fibroblast cells, and HEK293 human embryonic kidney cells were obtained from American Type Culture Collection (ATCC, Manassas, Va., USA). A549 cells were cultured in RPMI 1640 (WelGene) supplemented with heat-inactivated 10% FBS (WelGene), penicillin (100 units/mL), and streptomycin (100 μg/mL).

NIH/3T3 cells, HeLa cells, and HEK293 cells were cultured in DMEM (WelGene) supplemented with heat-inactivated 10% FBS (WelGene), penicillin (100 units/mL), and streptomycin (100 μg/mL). All the cell lines were maintained in a humidified atmosphere of 5% $CO_2$ and 95% air at 37° C. Two days before imaging, the cells were detached and $10^4$/$mm^2$ cells were plated on glass-bottomed dishes (MatTek).

For labeling, the growth medium was removed and replaced with serum-free RPMI 1640 (without D-glucose) (United Search Partners, Austin, Tex., USA).

The cells were treated and incubated with the required concentration of a tracker at 37° C. for 10 min.

Thereafter, the cells were washed three times with phosphate buffered saline (PBS; Gibco) and then imaged.

For comparison of the relative uptake of AG1 and AG2 per unit cell, the TPEF intensities from regions of interest were chosen without bias from among 40-60 cells as determined by the photomultiplier tube (PMT) and the data were digitalized using Histogram (a program for data analysis).

The relative tissue uptake was determined by the same method except that TPM images of the tissue sample were obtained at different depths.

The effects of taxol and combretastatin on the AG2 uptake were determined by adding an appropriate amount of the DMSO solution (10 mM) of the anti cancer agents to the cells and tissues.

In all cases the DMSO content was maintained to be 1%.

Experimental Example 5

Optimum Concentration of AG1 and AG2 for Uptake Experiment

In determine the optimum concentration for the uptake experiment, TPM images of A549 cells labeled for 30 min with 6, 12.5, 25, 50, and 100 μM of AG1 and AG2 were compared. The image appeared brighter as the probe concentration was increased up to 50 μM; however, at higher concentrations than this, cell death was observed.

Figure 3:
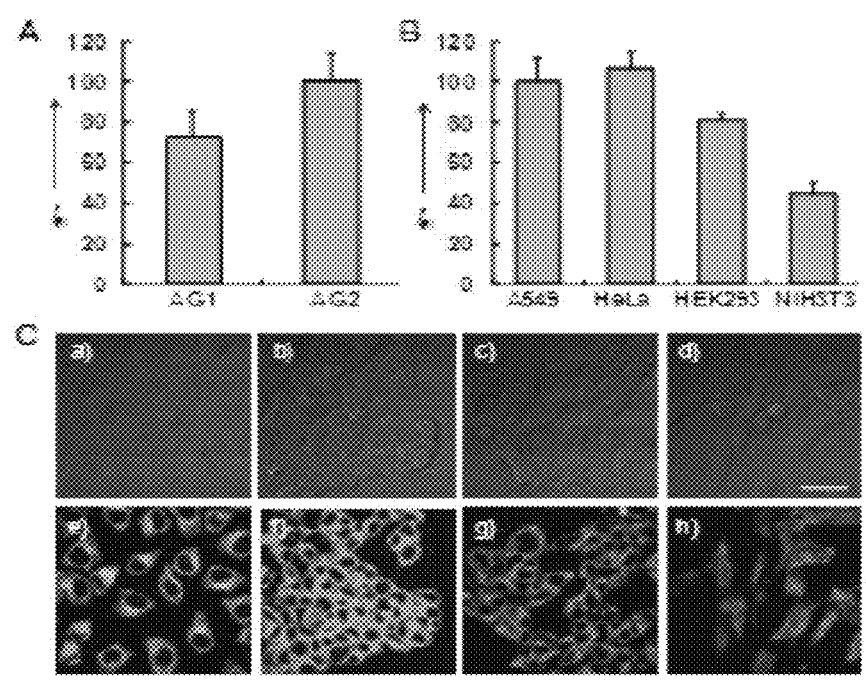
FIG. 3: (A) Relative AG1 and AG2 uptake by A549 cells. (B) Relative AG2 uptake by cancer cells (A549, HeLa) and normal cells (HEK293, NIH/3T3). TPEF intensities from 40-60 cells were determined by photomultiplier tube (PMT). The data are the average of at least five independent experiments. (C) TPM Images of A549 cells (a, e), HeLa cells (b, f), HEK293 cells (c, g), and NIH/3T3 cells (d, h) after AG2 uptake. a-d are bright-field images and e-j are TPM images. The images were obtained by collecting the TPEF in the range of 520-620 nm upon excitation with fs pulses at 780 nm. The images shown are representative of the images obtained in the repeated experiments (n=5). Scale bar, 30 μm.

Moreover, the uptake rate was faster (600 vs 800 s) and the TPM image was brighter when the cells were labeled with AG2 than when they were treated with AG1 (FIG. 3). Therefore, 50 μM of AG2 was used for the uptake experiments.

In order to confirm that the tracer couldn't affect the viability of A549 cells in the incubation condition, a CCK-8 kit (Cell Counting Kit-8, Dojindo, Japan) was used according to the manufacturer's protocol. The results are shown in FIG. 7.

Experimental Example 6

Colocalization Experiment

To determine where AG2 is predominantly located inside the cells, a colocalization experiment was conducted with A549 cells co-stained with AG2 and MitoTracker. MitoTracker is a well known one-photon fluorescent (OPF) probe for the mitochondria.

The TPM image was well merged with the OPM image, indicating that the probes are predominantly located in the mitochondria (FIG. 8).

Experimental Example 7

Competition Experiment for Uptake Pathway

To determine whether the intracellular uptake pathway of AG2 is relevant to that of D-glucose, a competition experiment was conducted.

To this end, A549 cells were incubated with AG2 (50 μM) for 10 min in the presence of 0, 10, and 50 mM D-glucose, and 50 mM L-glucose, and relative AG2 uptake was determined by TPM.

To confirm that the osmotic pressure does not have an influence on the uptake, the same experiment was conducted in the presence of 55 mM D, L-alanine. The results are shown in FIG. 9.

Experimental Example 8

Preparation and TPM Imaging of Human Cancerous Tissue Slices

Human colon cancer tissue and normal tissue were obtained from colon cancer patients by conducting colonoscopic examinations and taking samples.

Normal tissues, cancerous tissue, and cancerous tissue containing 50 μM taxol were incubated in artificial cerebrospinal fluid (ACSF) bubbled with 95% $O_2$ and 5% $CO_2$ for 4 hrs at 37° C. The tissues were then washed three times with ACSF, transferred to glass-bottomed dishes (MatTek), added with 50 μM AG2, and observed by TPM.

To determine whether the relative uptake was affected by incubation in ACSF, the same experiment was conducted with normal tissue and colon cancerous tissue obtained immediately after the colonoscopic biopsy. The results were similar to those obtained with tissue incubated in ACSF for 4 hrs, which indicates that the relative uptake is not influenced by the incubation (see FIGS. 10A-10D).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for screening an anticancer agent, comprising applying a two-photon tracer comprising a structure of the following Chemical Formula 5 or 6 to tissues in vivo or in vitro in combination with an anticancer agent, and monitoring the tracer with two-photon microscopy:

[Chemical Formula 5]

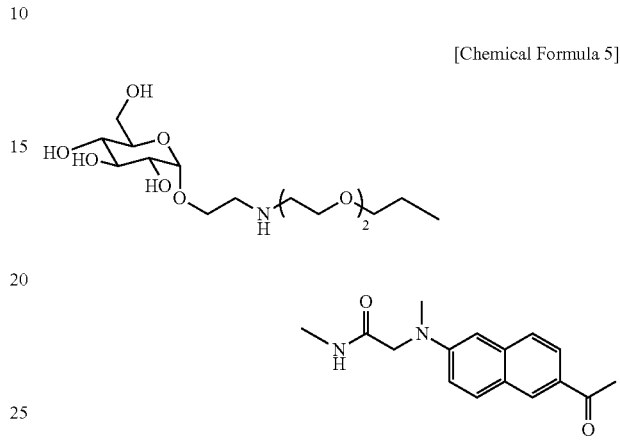

[Chemical Formula 6]

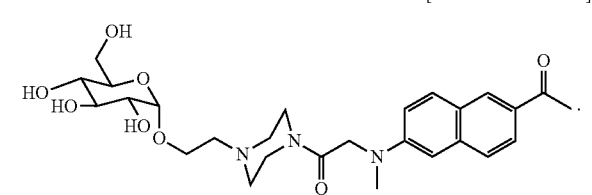

2. The method according to claim 1, wherein two-photon microscopy images are obtained at different depths from a surface of the tissue.

3. A method for diagnosing cancer cell, comprising:
adding a two-photon tracer comprising a structure of the following Chemical Formula 5 or 6 to cells in vivo or in vitro; and
detecting cellular uptake of the two-photon tracer by the cells with two-photon microscopy for determining whether the cells are cancer cells or not:

[Chemical Formula 5]

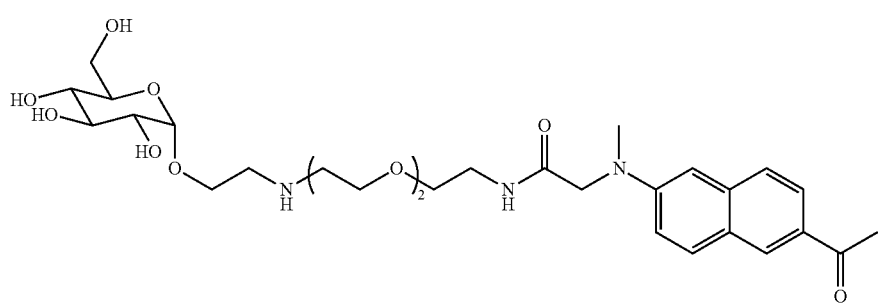

-continued
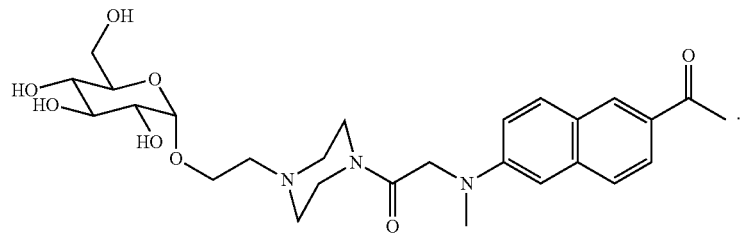
4. The method according to claim 3, wherein the cells are obtained from cancer in an early stage.